United States Patent [19]
Horodysky

[11] Patent Number: 4,581,039
[45] Date of Patent: Apr. 8, 1986

[54] DIAMINE CARBOXYLATES AND LUBRICANT AND FUEL COMPOSITIONS CONTAINING SAME

[75] Inventor: Andrew G. Horodysky, Cherry Hill, N.J.

[73] Assignee: Mobil Oil Corporation, New York, N.Y.

[21] Appl. No.: 741,392

[22] Filed: Jun. 5, 1985

Related U.S. Application Data

[62] Division of Ser. No. 535,140, Sep. 23, 1983, Pat. No. 4,537,694.

[51] Int. Cl.$^4$ ............................ C10L 1/18; C10L 1/22
[52] U.S. Cl. ............................................ 44/71; 44/53; 44/56
[58] Field of Search ............................... 44/71, 56, 53

[56] References Cited

U.S. PATENT DOCUMENTS

| | | | |
|---|---|---|---|
| 3,755,320 | 11/1973 | Vigo et al. | 44/63 |
| 3,907,704 | 9/1975 | Murphy | 44/71 |
| 4,374,741 | 2/1983 | Riesler | 252/51.5 A |
| 4,537,694 | 8/1985 | Horodysky | 252/51.5 A |

*Primary Examiner*—Jacqueline V. Howard
*Attorney, Agent, or Firm*—Alexander J. McKillop; Michael G. Gilman; Van D. Harrison, Jr.

[57] ABSTRACT

N-Hydrocarbyl hydrocarbylenediamine carboxylates, which can be made by the reaction of the appropriate diamine and organic monocarboxylic acid, demonstrate friction reducing properties when formulated into lubricants, particularly lubricating oils, and fuel consumption reduction properties when formulated into such lubricants or into fuels.

11 Claims, No Drawings

DIAMINE CARBOXYLATES AND LUBRICANT AND FUEL COMPOSITIONS CONTAINING SAME

This is a division of copending application Ser. No. 535,140 filed Sept. 23, 1983, now U.S. Pat. No. 4,537,694.

BACKGROUND OF THE INVENION

1. Field of the Invention

The invention relates to novel products and to their use in lubricants or liquid fuels to reduce friction and fuel consumption in internal combustion engine. More particularly, the invention relates to certain hydrocarbyl hydrocarbylenediamine carboxylates and to lubricant and fuel compositions containing same.

2. Discussion of Prior Related Disclosures

As those skilled in this art known, additives impart special properties to lubricants. They may give the lubricants new properties or they may enhance properties already present. One property all lubricants have in common is the reduction of friction between materials in contact. Nonetheless, the art constantly seeks new materials to enhance such friction properties.

A lubricant, even without additives, when used in an internal combustion engine, for example, will not only reduce friction, but in the process will also reduce consumption of the fuel required to run it. When oils appeared to be inexhaustable, and cheap, minimum attention was given to developing additives for the specific purpose of increasing frictional properties. Instead, most of the advances in this area came as a result of additives being placed in lubricants for other purposes. However, recent events have spurred research programs designed specifically to find materials capable of enhancing the ability of lubricant to reduce friction.

One of the more interesting facts discovered is that there is no absolute correlation between friction reducing properties of an additive and its ability to correspondingly further reduce fuel consumption in an engine. That is, one cannot predict with certainty, from the ability of an additive to reduce friction that it will also act to decrease fuel consumption. Thus, even though the use of amides in lubricants is known (see U.S. Pat. No. 3,884,822, for example, which discloses lubricants containing the product of reaction between an aminopyridine and oleic acid), no art teaches or suggests that the salts of this invention are useful for the purposes disclosed herein.

SUMMARY OF THE INVENTION

In accordance with the invention there is provided a lubricant liquid or fuel composition comprising a major proportion of a lubricant or fuel and an antifriction amount of a hydrocarbyl hydrocarbylenediamine carboxylate of the formula:

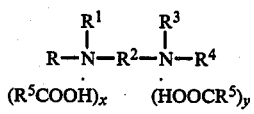

wherein R, $R^1$, $R^3$ and $R^4$ are hydrogen or a $C_6$ to $C_{20}$ hydrocarbyl group, at least one of R and $R^1$ being a hydrocarbyl group, $R^2$ is a $C_2$ to $C_4$ hydrocarbylene group, $R^5$ is a $C_6$ to $C_{20}$ hydrocarbyl group, x is 0 or 1 and y is 0 or 1, at least one of x and y being 1.

As used herein, "hydrocarbyl" and "hydrocarbylene" are preferably alkyl and alkylene, respectively, but may include alkenyl and alkenylene. "Hydrocarbyl" also may include aryl, alkaryl, aralkyl and cycloalkyl groups, the aryl portions having 6 to 14 carbon atoms.

The invention also provides the compounds per se and a method of reducing fuel consumption in internal combustion engines employing the disclosed compositions.

DESCRIPTION OF SPECIFIC EMBODIMENTS

The diamine carboxylates can be made simply by heating a mixture of diamine and organic monocarboxyl acid at a temperature and for a time to form the salt, but to prevent amide formation. In general, they can be made by reacting an appropriate diamine of the formula:

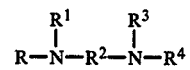

with an acid of the formula:

wherein R, $R^1$, $R^2$, $R^3$, $R^4$ and $R^5$ are as hereinabove described. Typical acids include stearic acid, isostearic acid, myristic acid, lauric acid, hydrogenated tall oil acids, oleic acid, linoleic acid, dodecanoic acid and the like.

The general reaction conditions are not critical. Reaction can take place between the diamine and the acid at a temperature of between about 20° C. and about 110° C., preferably about 40° C. to about 80° C. The reaction will usually be completed in from 1 to 10 hours, but where the reactants demand it, up to 24 hours may be required for reaction completion.

Hydrocarbon solvents, or other inert solvents may be used in the reaction. Included among the useful solvents are benzene, toluene and xylene. In general, any hydrocarbon solvent can be used in which the reactants are soluble and which can, if the products are soluble therein, by easily removed.

In carrying out the reaction, the molar ratio of diamine to acid preferably will range from about 1:1 to aboud 1:2.

Some of the useful diamines include nonyl-1,3-propylenediamine, decyl-1,3-propylenediamine, undecyl-1,3-propylenediamine, dodecyl-1,3-propylenediamine, tridecyl-1,3-propylenediamine, pentadecyl-1,3-propylenediamine, hexadecyl-1,3-propylenediamine, stearyl-1,3-propylenediamine, oleyl-1,3-propylenediamine, coco-1,3-propylenediamine, soya-1,3-propylenediamine and mixtures of two or more of these. All the R groups mentioned are alkyl. Others, such as an aryl group, an alkaryl group, an aralkyl group or a cycloalkyl group, as previously mentioned, may be used in effective additives.

An important feature of the invention is the ability of the additives to improve the friction qualities of oleaginous materials such as lubricating oils, which may be either a mineral oil a synthetic oil, or mixtures thereof, or a grease in which any of the aforementioned oils are employed as the vehicle. In general, mineral oils, both paraffinic, naphthenic or mixtures thereof, are employed as a lubricating oil or as the grease vehicle, they may be of any suitable lubricating viscosity range, as for example, from about 45 SSR at 100° F. to about 6000 SSU at 100° F., and preferably from about 50 to about 250 SSR at 210° F. These oils may have viscosity indexes ranging to about 100 or higher. Viscosity indexes from about 70 to about 95 are preferred. The average molecular weights of these oils may range from about 250 to about 800. Where the lubricant is to be employed in the form of grease, the lubricating oil is generally employed in an amount sufficient to balance the total grease composition, after accounting for the desired quantity of the thickening agent, and other additive components to be included in the grease formulation. A wide variety of materials may be employed as thickening or gelling agents. These may include any of the conventional metal salts or soaps, which are dispersed in the lubricating vehicle in grease-forming quantities in an amount to impart to the resulting grease composition the desired consistency. Other thickening agents that may bea employed in the grease formulation may comprise the non-soap thickeners, such as surface-modified clays and silicas, aryl ureas, calcium complexes and similar materials. In general, grease thickeners may be employed which do not melt and dissolve when used at the required temperature within a particular environment; however, in all other respects, any material which is normally employed for thickening or gelling hydrocarbon fluids for forming grease can be used in preparing the aforementioned improved grease in accordance with the present invention.

In instances where synthetic oils are desired, various classes of oils may be successfully utilized. Typical synthetic vehicles include polyisobutylenes, polybutenes, hydrogenated polydecenes, polypropylene glycol, polyethylene glycol, trimethylol propane esters, neopentyl and pentaerythritol esters, di(2-ethylhexyl)-sebacate, di(2-ethylhexyl)adipate, dibutyl phthalate, fluorocarbons, silicate esters, silanes, esters of phosphorus-containing acids, liquid ureas, ferrocene derivatives, hydrogenated synthetic oils, chain-type polyphenyls, siloxanes and silicones (polysiloxanes) and alkyl-substituted diphenyl ethers typified by a butyl-substituted bis(p-phenoxy phenyl)ether, phenoxy phenylethers. In preparing greases using synthetic oils, thickeners known to the art (including some of those mentioned hereinabove) can be used.

It is to be understood that the compositions contemplated herein can also contain other materials. For example, other corrosion inhibitors, extreme pressure agents, viscosity index improvers, coantioxidants, antiwear agents and the like can be used. These include, but are not limited to, phenates, sulfonates, succinimides, zinc dialkyl dithiophosphates, and the like. These materials do not detract from the value of the compositions of this invention; rather the materials serve to impart their customary properties to the particular compositions in which they are incorporated.

The products of this invention can also be employed in liquid hydrocarbon fuels, alcohol fuels or mixtures thereof, including mixtures of hydrocarbons, mixtures of alcohols and mixtures of hydrocarbon and alcohol fuels. About 25 pounds to about 500 pounds or preferably about 50 to 100 pounds of etherdiamine amide per thousand barrels of fuel for internal combustion engines may be used. Liquid hydrocarbon fuels include gasoline, fuel oils and diesel oils. Methyl and ethyl alcohols are examples of alcohol fuels. Other additives, such as fuel dispersants, antirust agents, demulsifiers, metal deactivators and the like can be used with our friction reducers in various fuel formulations.

In general, the reaction products of the present invention may be employed in any amount which is effective for imparting the desired degree of friction reduction or antioxidant activity. In these applications, the product is effectively employed in amounts from about 0.1% to about 10% by weight, and preferably from about 1% to about 5% of the total weight of the composition.

The following Examples will present illustrations of the invention. They are illustrative only, and are not meant to limit the invention.

EXAMPLE 1

N-Oleyl-1,3-Propylenediamine Dioleate

Approximately 720 g of N-oleyl-1,3-propylenediamine (obtained commercially as Duomeen O from Armak Chemical Co.) was reacted with 1100 g of oleic acid for 1 hour with agitation at about 55°–60° C.

EXAMPLE 2

N-Coco-1,3-Propylenediamine Dioleate

Approximately 582 g of N-coco-1,3-propylenediamine (obtained commercially as Duomeen C from Armak Chemical Co.) was reacted with 560 g of oleic acid for 1 hour at about 60°–65° C. with agitation.

EXAMPLE 3

N-Oleyl-1,3-Propylenediamine Diisosterate

Approximately 180 g of N-oleyl-1,3-propylenediamine (obtained commercially as Duomeen O from Armak Chemical Co.) was reacted with 310 g of isostearic acid for ½ hour at about 60° C. with agitation.

EXAMPLE 4

N-Oleyl-1,3-Propylenediamine Monooleate

Approximately 288 g of N-oleyl-1,3-propylenediamine (obtained commercially as Duomeen O from Armak Chemical Co.) was reacted with 224 g of oleic acid for ½ hour at about 60° C. with agitation.

EVALUATION OF THE COMPOUNDS

The compounds were evaluated in Low Velocity Friction Apparatus (LVFA) in a fully formulated mineral or synthetic, automotive engine oil containing an additive package including antioxidant, dispersant and detergent.

Although evaluation of additives was performed in lubricant formulations, these results correlate well with expected frictional and fuel economy improvements when these same additives are used in fuels burned in internal combustion engines. For example, this test predicts the reduction in friction of the piston rings moving against the cylinder walls that have been wetted by the additive blended into the fuel.

Description

The Low Velocity Friction Apparatus (LVFA) is used to measure the coefficient of friction of test lubricants under various loads, temperatures, and sliding speeds. The LVFA consists of a flat SEA 1020 steel surface (diameter 1.5 in.) which is attached to a drive shaft and rotated over a stationary, raised, narrow ringed SAE 1020 steel surface (area 0.08 in.$^2$. Both surfaces are submerged in the test lubricant. Friction between the steel surfaces is measured as a function of the sliding speed at a lubricant temperature of 250° F. The friction between the rubbing surfaces is measured using a torque arm-strain gauge system. The strain gauge output, which is calibrated to be equal the the coefficient of friction, is fed to the Y axis of an X-Y plotter. The speed signal from the tachometer-generator is fed to the X-axis. To minimize external friction, the piston is supported by an air bearing. The normal force loading the rubbing surfaces is regulated by air pressure on the bottom of the piston. The drive system consists of an infinitely variable-speed hydraulic transmission driven by a ½ HP electric motor. To vary the sliding speed, the output speed of the transmission is regulated by a lever-cammotor arrangement.

Procedure

The rubbing surfaces and 12–13 ml of test lubricants are placed on the LVFA. A 240 psi load is applied and the sliding speed is maintained at 40 fpm at ambient temperature for a few minutes. A plot for coefficients of friction ($U_k$) vs. speed were taken at 240, 300, 400, and 500 psi. Freshly polished steel specimens are used for each run. The surface of the steel is parallel ground to 4 to 8 microinches. The results in Table 1 refer to percent reduction in friction compared to the unmodified oil. That is, the formulation mentioned above was tested without the compound of this invention and this became the basis for comparison. The results were obtained at 250° F. and 500 psi.

TABLE 1

| Example No. | Additive Conc. Wt. % | Reduction or % Change in Coefficient of Friction | |
|---|---|---|---|
| | | 5 Ft./Min. | 30 Ft./Min. |
| Base Oil (fully formulated synthetic engine oil containing detergent/dispersant/inhibitor package) SAE 5W-30 | — | 0 | 0 |
| Example 1 in Base Oil | 2 | 46 | 32 |
| | 1 | 32 | 24 |
| Example 2 in Base Oil | 2 | 41 | 25 |
| Example 4 in Base Oil | 2 | 53 | 42 |

TABLE 2

| Example No. | Additive Conc. Wt. % | Reduction or % Change Coefficient of Friction | |
|---|---|---|---|
| | | 5 Ft./Min. | 30 Ft./Min. |
| Base Oil (fully formulated engine oil containing detergent/dispersant/inhibitor package) SAE 10W-40 | — | 0 | 0 |
| Example 1 in Base Oil | 2 | 47 | 35 |
| | 1 | 42 | 24 |
| Example 3 in Base Oil | 2 | 32 | 31 |
| Example 4 in Base Oil | 2 | 53 | 42 |

The coefficients of friction were vastly reduced relative to both base oils. Reductions in the coefficients of friction of from about 30% to 40% were noted with the use of only 1% of Example 1 admixed into a fully formulated mineral or synthetic oil lubricant. Lower concentrations of less than 1% are also expected to substantially reduce friction in such oils.

I claim:

1. A liquid fuel composition comprising a major portion of a liquid fuel and an antifriction amount of a compound of the formula

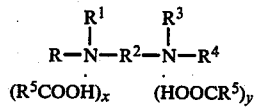

wherein R, $R^1$, $R^3$ and $R^4$ with the N groups making up a diamino group are hydrogen or a $C_6$ to $C_{20}$ hydrocarbyl group, at least one of R and $R^1$ being a hydrocarbyl group, $R^2$ is a $C_2$ to $C_4$ hydrocarbylene group, $R^5$ is a component of at least one acid group and is a $C_6$ to $C_{20}$ hydrocarbyl group, x is 0 or 1 and y is 0 or 1, at least one of x and y being 1.

2. The composition of claim 1 wherein the hydrocarbyl group is selected from the group consisting of alkyl, alkenyl, aryl, alkaryl, aralkyl and cycloalkyl groups.

3. The composition of claim 1 wherein the hydrocarbyl group is selected from the group consisting of alkyl, alkenyl, aryl, alkaryl, aralkyl and cycloalkyl groups.

4. The composition of claim 1 wherein the diamine group is selected from the group consisting of nonyl-, decyl-, undecyl-, dodecyl-, tridecyl-, pentadecyl-, hexadecyl-, stearyl-, oleyl-, coco-, tallow and soya-1,3-propylenediamine.

5. The composition of claim 1 wherein the acid group is selected from the group consisting of stearic, isostearic, myristic, lauric, hydrogenated tall oil, oleic, linoleic and dodecanoic acid.

6. The composition of claim 1 wherein the compound has the formula

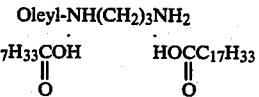

7. The composition of claim 1 wherein the compound has the formula

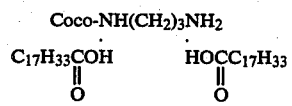

8. The composition of claim 1 wherein the compound has the formula

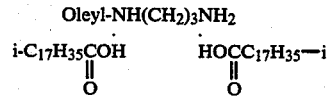

9. The composition of claim 1 wherein the compound has the formula

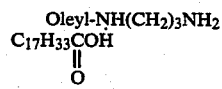

or

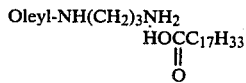

10. The composition of claim 1 wherein the liquid fuel is a diesel oil, a fuel oil, a gasoline or an alochol or a mixture of gasoline and alcohol.

11. A method for decreasing fuel consumption in an internal engine by fueling same with a composition comprising a major proportion of liquid fuel and an antifriction amount of a compound of the formula

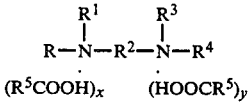

wherein R, $R^1$, $R^3$ and $R^4$ are hydrogen or a $C_6$ to $C_{20}$ hydrocarbyl group, at least one of R and $R^1$ being a hydrocarbyl group, $R^2$ is a $C_2$ to $C_4$ hydrocarbylene group, $R^5$ a $C_6$ to $C_{20}$ hydrocarbyl group, x is 0 or 1 and y is 0 or 1, at least one of x and y being 1.

* * * * *